United States Patent [19]

Ko et al.

[11] Patent Number: 4,688,580
[45] Date of Patent: Aug. 25, 1987

[54] NON-INVASIVE ELECTROMAGNETIC TECHNIQUE FOR MONITORING BONE HEALING AND BONE FRACTURE LOCALIZATION

[75] Inventors: Harvey W. Ko; Lynn W. Hart, both of Columbia, Md.

[73] Assignee: The Johns Hopkins University, Baltimore, Md.

[21] Appl. No.: 753,824

[22] Filed: Jul. 11, 1985

[51] Int. Cl.⁴ ............................................. A61B 5/05
[52] U.S. Cl. .................................... 128/734; 128/653
[58] Field of Search ................. 128/419 F, 734, 653, 128/1.3–1.5, 630; 324/236, 237, 327, 332, 333

[56] References Cited

U.S. PATENT DOCUMENTS

| 3,597,687 | 8/1971 | Seipp | 324/236 |
| 3,719,882 | 3/1973 | Pincus | 324/236 |
| 3,808,524 | 4/1974 | Tarassoff et al. | 324/236 |
| 3,931,571 | 1/1976 | Hocking et al. | 324/236 |
| 4,048,986 | 9/1977 | Ott | 128/660 |
| 4,548,208 | 10/1985 | Niemi | 128/419 F |

FOREIGN PATENT DOCUMENTS 2842203 4/1980 Fed. Rep. of Germany ...... 128/653
1033128 8/1983 U.S.S.R. ............................. 128/653

OTHER PUBLICATIONS

Jupe, "Crack Detector for Production Testing", Electronics Oct. 1945, pp. 114–115.

Owston, "A High Frequency Eddy-Current Non-Destructive Testing Apparatus With Automatic Probt Positioning Suitable for Scanning Applications", Journal of Physics E: Scientific Instruments 1970, vol. 3, pp. 814–818.

Ogren, "Sensor Circuit Utilizing Variable Inductance Input", IBM Technical Disclosure, vol. 14, No. 4, Sep. 1971.

Primary Examiner—Kyle L. Howell
Assistant Examiner—Ruth S. Smith
Attorney, Agent, or Firm—Robert E. Archibald; Howard W. Califano

[57] ABSTRACT

An apparatus and method for non-invasive sensing of bone healing is disclosed. The apparatus and method uses an electromagnetic field to measure impedance changes at the bone fracture site during the healing process. The impedance change at the fracture site is a direct indication of the mechanical strength of the fracture site.

13 Claims, 7 Drawing Figures

NON-INVASIVE ELECTROMAGNETIC TECHNIQUE FOR MONITORING BONE HEALING AND BONE FRACTURE LOCALIZATION

STATEMENT OF GOVERNMENTAL INTEREST

The Government has rights in this invention pursuant to Contract No. N00024-85-C-5301 awarded by the Department of the Navy.

BACKGROUND OF THE INVENTION

1. Field of the Invention

The invention relates to a method and apparatus for locating a fracture site in a human or animal bone and for measuring the increase in mechanical strength at the fracture site during the healing process. More particularly, the invention uses an electromagnetic field to non-invasively measure impedance changes at a bone fracture site during the healing process.

2. Description of the Prior Art

Currently the prior art does not teach an effective method or apparatus for measuring non-invasively the mechanical strength of a bone fracture during the healing process. X-ray techniques are of some assistance but fail to quantitatively indicate mechanical strength. In most cases, a physician maintains the broken bone in a cast for what is conservatively a sufficiently long time for mechanical strength to return to the fracture site. However, such a technique is inadequate for certain patients, including the elderly, who have a healing process which proceeds at an unknown rate which is however slower than normal. Similarly, it would be advantageous to have an early removal of a cast so that the patient could return to normal activities. This would be particularly true of athletes who could return to normal professional activities as soon as adequate mechanical strength had returned to the fracture site.

As will be discussed in detail subsequently in this application, Applicants have related the impedance change at a fracture site with changes in mechanical strength during the healing process. To non-invasively detect such an impedance change, Applicants have invented a method and apparatus which uses an electromagnetic field for sensing such an impedance change at the fracture site. U.S. Pat. No. 3,735,245 entitled "Method and Apparatus for Measuring Fat Content in Animal Tissue Either in Vivo or in Slaughtered and Prepared Form" invented by Wesley H. Harker, teaches that the fat content in meat can be determined by measuring the impedance difference between fat and meat tissue. The Harker apparatus determines gross impedance change and does not provide adequate spatial resolution for the present use. U.S. Pat. No. 4,240,445 teaches the use of an electromagnetic field responsive to the dielectric impedance of water to detect the presence of water in a patient's lungs. However, such an apparatus does not detect the conductivity variations required in the present invention. U.S. Pat. No. 3,789,834 relates to the measurement of body impedance by using a transmitter and receiver and computing transmitted wave impedance from the electrical or magnetic field generated. However, the antenna pickup would receive extraneous noise rendering it inappropriate for the present use. None of the above cited references contemplate measuring the mechanical strength of a bone by measuring the impedance change along a fracture site, and none of the references teach an apparatus capable of specifically detecting such impedance changes.

SUMMARY OF THE INVENTION

The present inventors realized through experimentation that the impedance change at the fracture site of a bone could be related to the extent of the fracture and to the degree of healing. They discovered that the electrical impedance of the bone at the fracture site increases with the extent of a transverse bone fracture. Further, this invention is based upon measuring mechanical strength of the bone fracture by quantitatively measuring the impedance change at the fracture site.

The present inventors also realize that the impedance change at the fracture site could be sensed non-invasively using a magnetic field and detecting the change in mutual inductance. The basic sensor utilizes a thin or narrow magnetic field coil winding which spatially concentrates the magnetic field and detects the impedance change at the fracture site. As a limb is passed within the proximity of the spatially discrete coil detector, the mutual inductance of the coil is detected and produces a change in the resonant amplitude and resonant frequency of the detection oscillator. The invented apparatus is capable of detecting small variations in impedance changes and quantitatively measuring such changes. The oscillator detector in combination with the magnetic coil is specifically designed to be sensitive to small impedance changes and to reduce polarization effects and background noise which could render such monitoring impossible.

A first novel feature of the invention is the method of detecting a bone fracture by measuring impedance changes at the fracture site.

A second novel feature of the invention is a means for non-invasively measuring mechanical strength of a bone fracture during the healing process by quantitatively measuring changes in impedance at the fracture site.

A third novel feature of the invention is the use of a coil winding and oscillator detector to detect changes in the impedance at the fracture site by noting changes in resonant frequency and resonant amplitude caused by changes in mutual inductance.

A fourth novel feature of the invention is a coil winding which is specifically designed to provide sufficient spatial resolution so that changes in impedance along a thin fracture site can be observed.

A fifth novel feature of the invention is the use of a coiled winding and an oscillator detector to detect small changes in impedance and which is adapted to quantitatively display such changes in impedance by displaying changes in the resonant frequency and resonant amplitude of the oscillator detector.

DETAILS OF DESCRIPTION OF THE EMBODIMENT

The present invention is based on the Applicants' discovery that the electrical impedance of the bone at a fracture site increases with the extent of a transverse bone fracture. Further, the healed fracture has a different impedance from the original bone and the impedance change is proportional to the mechanical strength of the bone. The present invention is directed to a non-invasive method and apparatus for measuring the local impedance at the site of the bone fracture.

Figure 1:
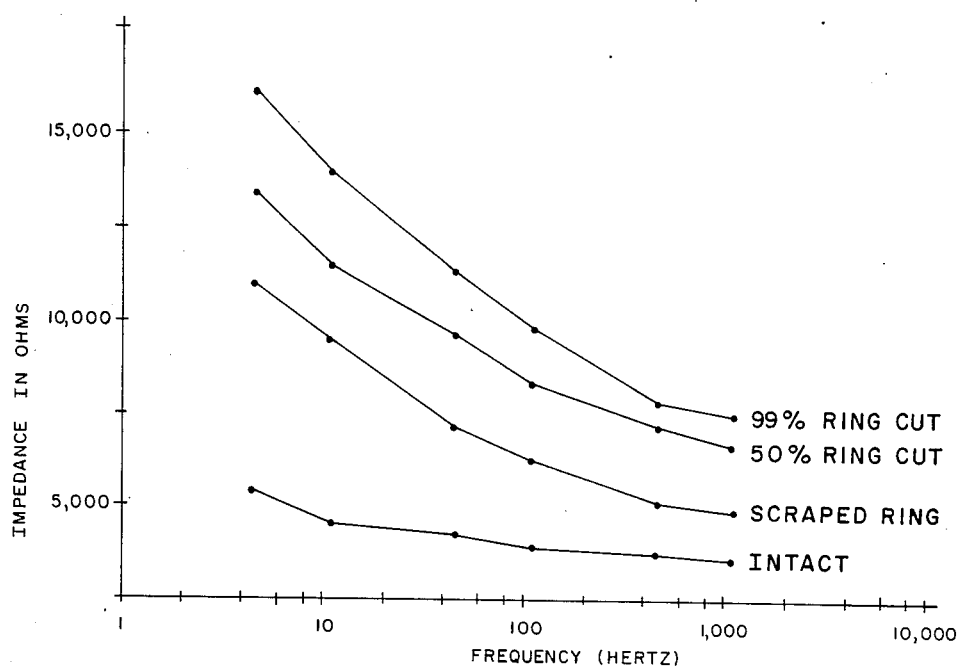
FIG. 1 is a graph showing bone impedance changes of the tibia as a function of frequency and extent of fracture.
Figure 2:
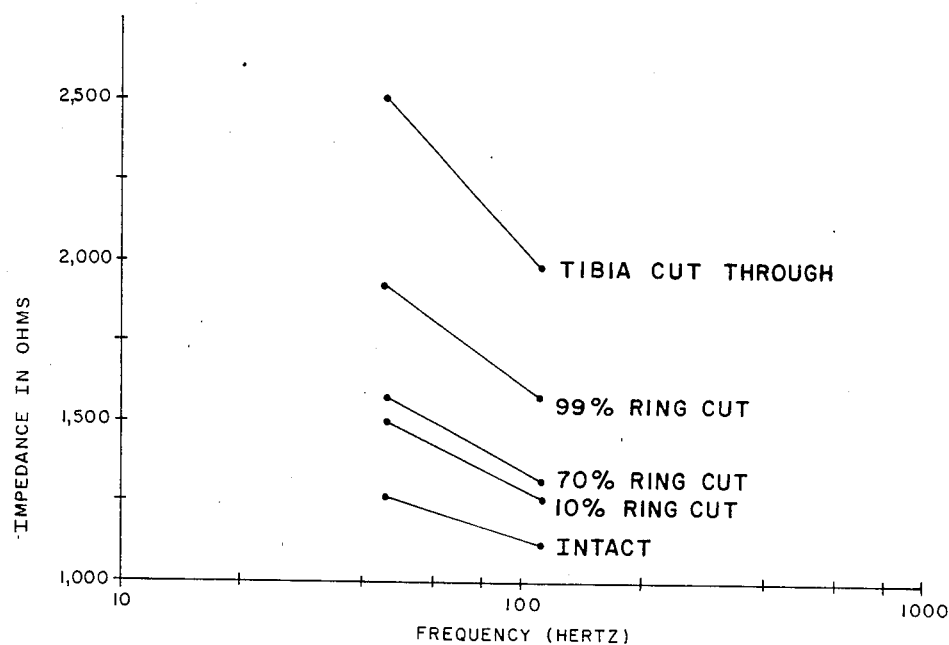
FIG. 2 is a graph showing the bone impedance changes for the tibia, with the fibula attached, as a function of frequency and extent of fracture.

FIGS. 1 and 2 show some of the initial impedance measurements of a fractured cadaver tibia. An initial invasive method was used wherein stainless steel electrodes were installed near both ends of the tibia so that the bone could be made part of a series circuit for measuring both bone impedance and the non-linearities of the impedance as a function of the degree of bone fracture. Transverse ring cuts were made circumferentially around the bone to simulate a bone fracture, and the cut bones were saturated in a saline solution. FIGS. 1 and 2 show that the electrical impedance of the bone increases with the extent of transverse fracture.

Figure 3:
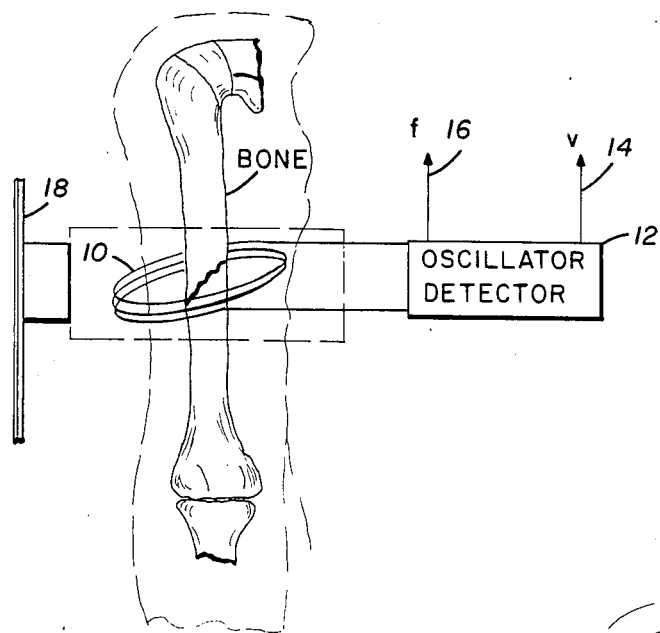
FIG. 3 is a block diagrammatic illustration of the present invention showing the use of a thin coil detector.
Figure 4:
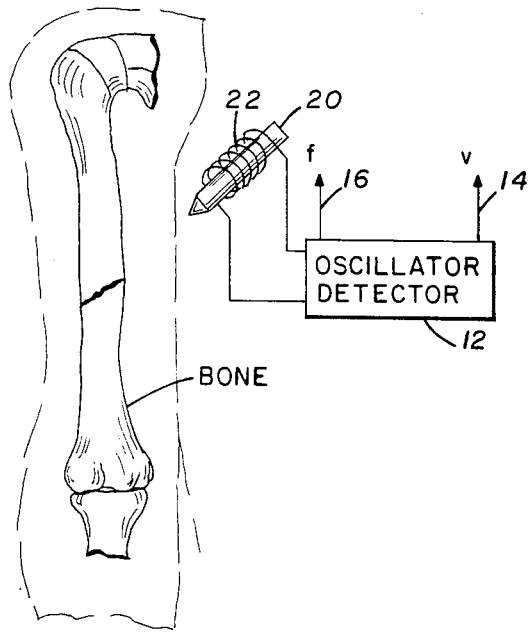
FIG. 4 is a block diagrammatic illustration of the present invention showing a wand magnetic detector which increases spatial resolution of the sensor system.

FIGS. 3 and 4 show a schematic representation of a non-invasive apparatus as taught by the present invention. The basic sensor is a thin or narrow magnetic field coil winding 10 which detects the presence of matter of different electrical productivity. The apparatus uses the same principle as some metal detectors which are used at the airport. As the conducting material passes within the proximity of the coil detector, the mutual inductance of the coil in the electronic circuit changes the frequency of oscillation of the detector circuit. The amount of oscillation is proportional to the value of the electrical conductivity passing through the detector coil. The magnetic field of the coil creates an electric field. The electric field creates induced eddy currents within the conducting bone material. These induced eddy current re-radiate a magnetic signal, which is detected by the detector coil. The amount of magnetic field which is re-radiated is proportional to the amount of eddy current which is induced. The amount of eddy current which is induced is proportional to the electrical conductivity of the bone.

Returning to FIG. 3, a broken limb would be passed through detector coil 10 which non-invasively ascertains the electrical conductivity in that section of the arm contained in the coil. Oscillator detector 12 is connected to the coil 10 and generates an oscillating magnetic signal in the coil. The change in mutual inductance of the coil is picked up by oscillator detector and results in a change in output 16 indicating a frequency change and output 14 indicating a voltage change. The extent of electrical conductivity of the bone is proportional to the degree of the fracture healing. The impedance change that coincides with the fracture healing process will vary from a high impedance of 20K ohms to a lower impedance of 0.01 ohm. Therefore, if a fresh fracture is measured, the electrical impedance is expected to be high; that is, the conductivity will have a low value. As the fracture heals, the electrical impedance will diminish and the electrical conductivity will increase. In this embodiment the detector coil 10 could operably slide on a track 18, so that linear displacement along the bone can be measured.

Alternatively, the embodiment shown in FIG. 4 could be used. In this embodiment coil 20 is wrapped around a magnetic core 22 to concentrate the magnetic flux lines. The slide or wand arrangement (18, 22) is operably moved across the fracture site at outputs (14, 16) are monitored.

It is expected that irradiation caused by the magnetic field will cause no harm to the patient.

Figure 5:
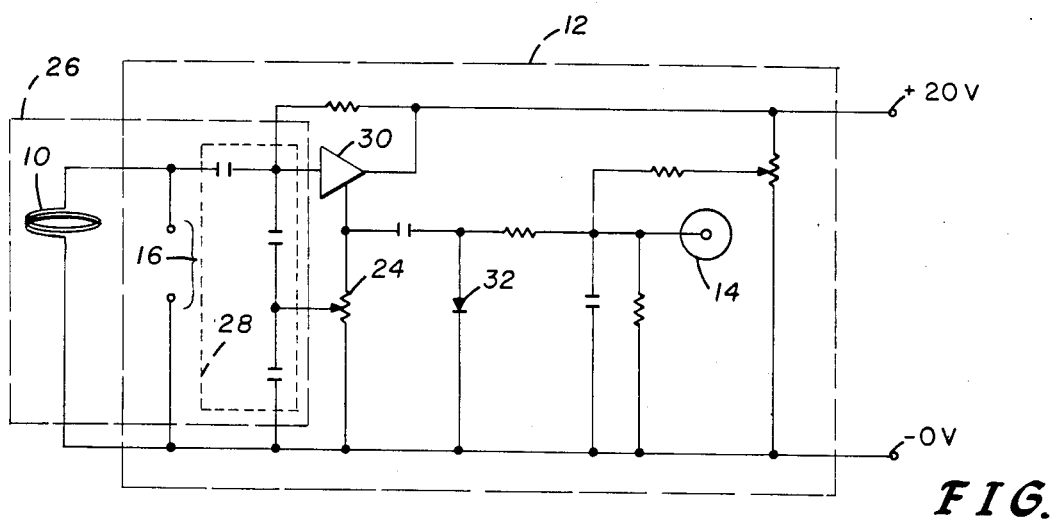
FIG. 5 is a schematic diagram of a typical circuit used in the present invention.

FIG. 5 is a schematic drawing of one possible circuit configuration for oscillator detector 12. Electronically, the circuit represents a marginally stable Colpitts oscillator whose frequency of oscillation is determined by the tank circuit. Although a Hartley-type oscillator, or similar, would work equally well. The potentiometer tap 24 helps to find the proper circuit resistance external to the tank circuit 26 resistance needed for stable oscillation. The tank circuit 26 includes coil 10 and capacitors 28. The transistor 30 with negative feedback provides stable voltage gain. A DC output 14 is extracted from the demodulator diode 32 which reflects the change in oscillator amplitude. The frequency is measured directly off coil 10 at output 16. When a bone is placed through coil 10, eddy currents are induced by the time changing magnetic field generated by the coil. The eddy currents in turn produced a secondary, though slight, magnetic field whose associated flux is coupled back to the coil. This produces a change in the coil impedance which changes the resonant amplitude, measured at output 14, and the resonant frequency, measured at output 16, of tank circuit 26. The coil inductances are in the millihenry (mH) range so that resonant frequencies in the hundreds of kHz to several MHz are obtained. In this frequency range, the impedance changes are dominated by conductivity properties and not polarization effects caused by the relative permittivity of the media.

Figure 6:
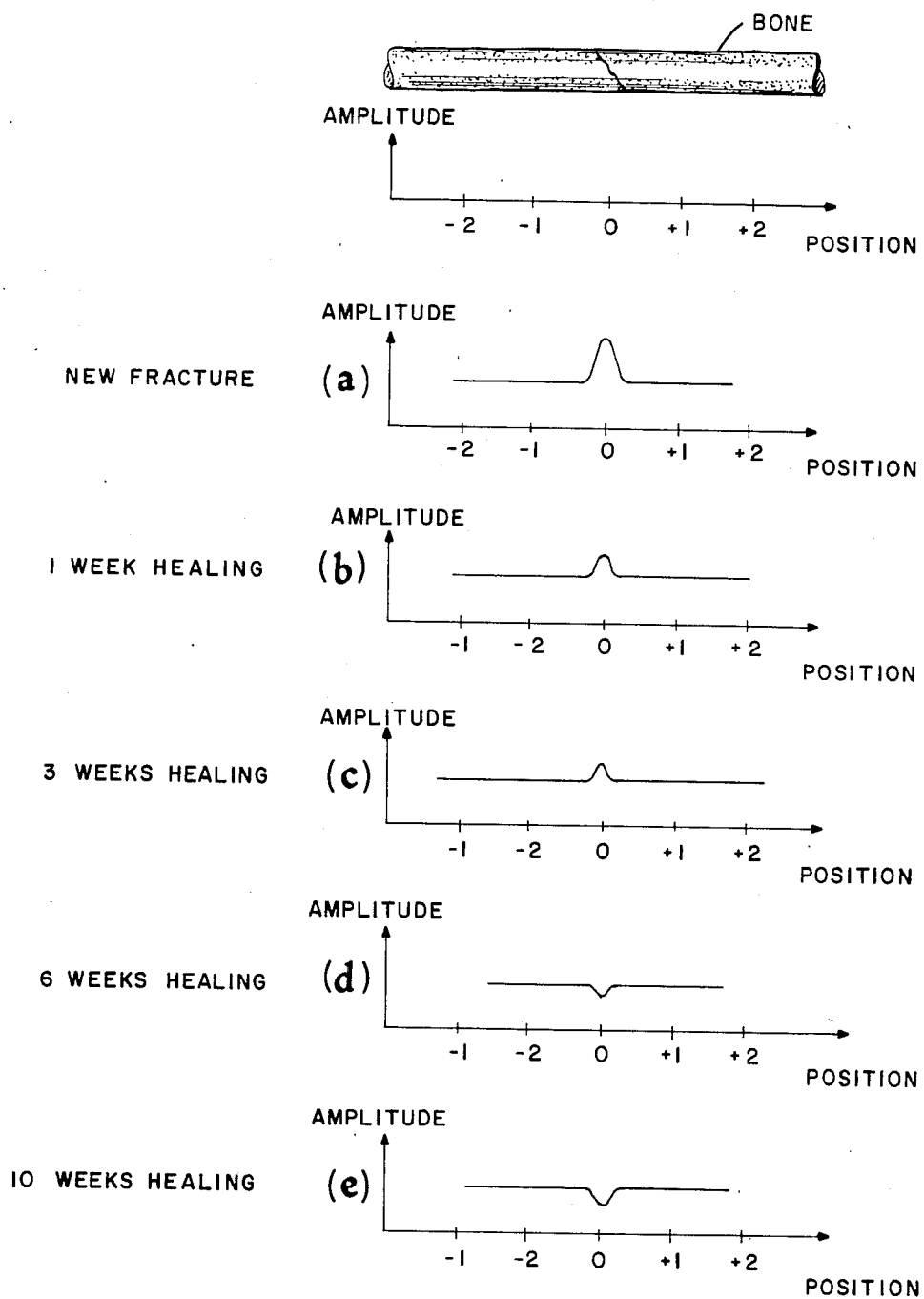
FIG. 6 is a family of graphs showing the change in resonant amplitude as a function of spatial displacement along the bone and as a function of time since the occurrence of the fracture.

FIG. 6 illustrates a change in resonant amplitude, measured at output 14, during the bone healing process. For a fresh fracture (FIG. 6a), the resonant amplitude at the fracture site is high indicating that electrical impedance at the fracture site is also high. As healing progresses (FIGS. 6b, c), the resonant amplitude decreases to a value associated with the impedance of unbroken bone. However, as the fracture site strengthens (FIGS. 6d, e) a change in polarity in the resonant amplitude occurs.

Figure 7:
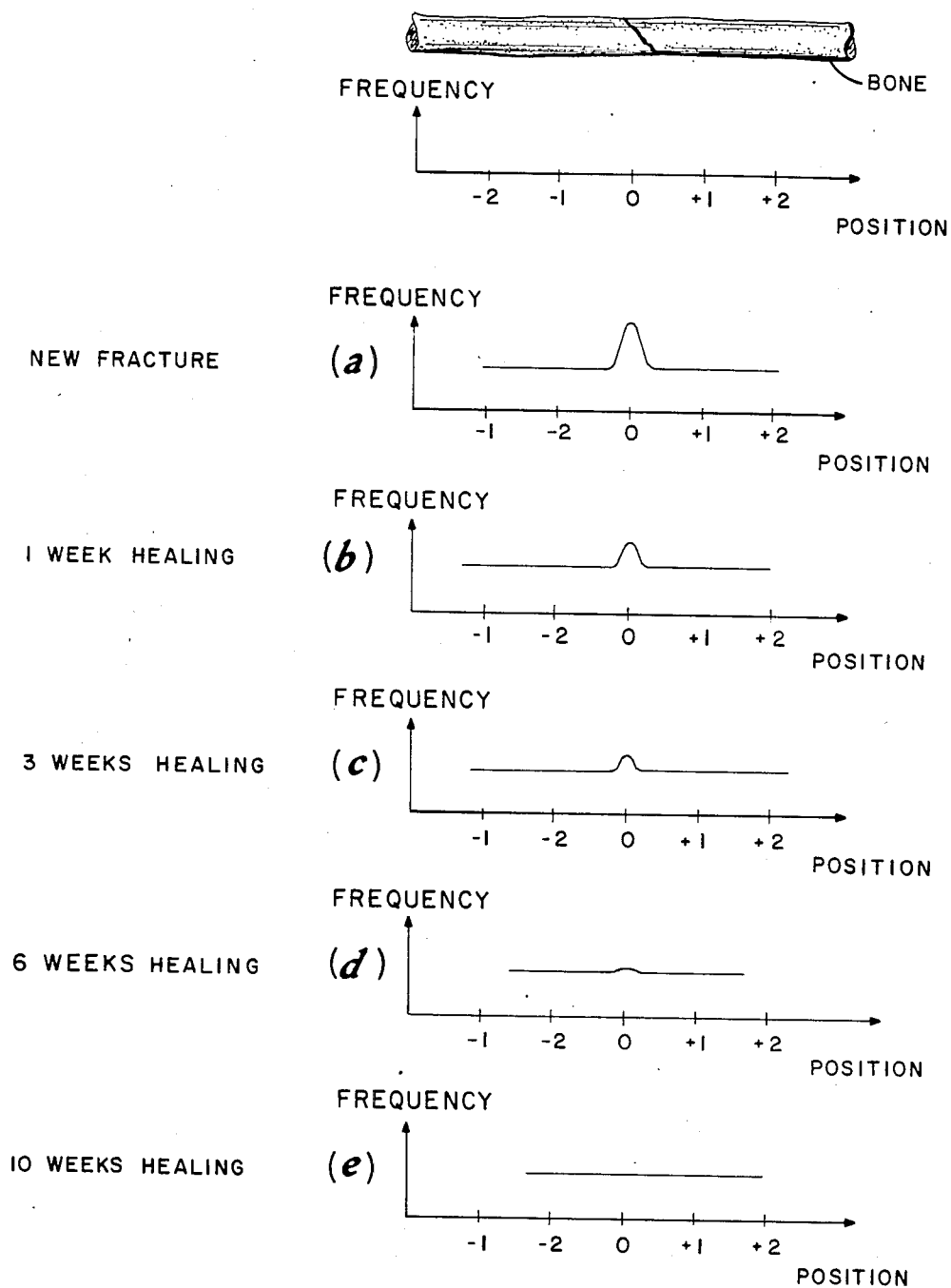
FIG. 7 is a family of graphs showing the change in resonant frequency as a function of spatial displacement along the bone and as a function of time since the occurrence of the fracture.

FIG. 7 illustrates a change in the resonant frequency, measured at output 16 during the bone healing process. For a fresh fracture (FIGS. 7, 8), the resonant frequency at the fracture site is high indicating a high electrical impedance. As healing progresses (FIGS. 7b-e), the resonant frequency will decrease until it has a value similar to the resonant frequency of unbroken bone.

Obviously many modifications and variations of the present invention are possible in light of the above teachings. It is therefore to be understood that within the scope of the appended claims the invention may be practiced otherwise than is specifically described.

What is claimed is:

1. A method for monitoring bone healing, comprising the steps of:
   noninvasively measuring the impedance of bone and other biological material in the region of a bone fracture site at a plurality of different times; and,
   comparing said impedance measurements to monitor healing of the bone fracture, wherein a healed fracture will have a lower impedance than a newly formed fracture site,
   and wherein noninvasively measuring impedance for each of said plurality of times comprises the following steps:
   generating an oscillating near field magnetic flux that is spatially concentrated in the region of the bone fracture site thereby producing eddy currents in bone and other biological matter located in the region of the bone fracture site, such eddy currents inducing a secondary magnetic emission which varies in response to the impedance of said bone and other biological matter located in the region of said fracture site; and, detecting said induced secondary magnetic emission and displaying an informational signal indicating the local impedance in the region of the fracture site.

2. A method of bone fracture localization, comprising the steps of:
   noninvasively measuring the impedance of bone and other biological matter at a plurality of localized regions along a bone; and,
   comparing said impedance measurements to determine the location of a higher impedance region indicating a fracture site on said bone, wherein said noninvasively measuring impedance for each of said plurality of regions comprises the following steps:
   generating a spatially concentrated oscillating near field magnetic flux along a region of said bone to induce eddy currents in bone and other biological matter within said region, such eddy currents inducing a secondary magnetic emission which varies in response to the impedance of bone and other biological matter within said region; and,
   detecting said induced secondary magnetic emission and displaying an informational signal indicating the impedance detected at said region.

3. A method for monitoring bone healing, comprising the steps of:
   noninvasively measuring the impedance of bone and other biological material in the region of a bone fracture site at a plurality of different times; and
   comparing said impedance measurements to monitor healing of the bone fracture, wherein a healed fracture will have a lower impedance than a newly formed fracture site, and wherein noninvasively measuring impedance for each of said plurality of times comprises the following steps:
   producing an oscillating magnetic field that is spatially concentrated in the region of the fracture site using a coil means, whereby eddy currents induced in bone and other biological matter will induce a secondary magnetic emission which alters the mutual inductance of said coil means in accordance with the impedance of bone and other biological matter in said region of the fracture site; and,
   detecting a change in said mutual inductance of said coil means, wherein an increase in mutual inductance indicates an increase in impedance and a decrease in mutual inductance indicate a decrease in impedance.

4. The method of claim 3, wherein said producing step comprises the step of exciting said coil means at a resonant frequency using an oscillator means and wherein said detecting step comprises the step of detecting changes in resonant amplitude caused by variations in said mutual inductance.

5. The method of claim 4, wherein said comparing step involves comparing the resonant amplitude detected at a first time with the resonant amplitude detected at a second later time wherein the resonant amplitude will decrease with a decrease in impedance.

6. The method of claim 4, wherein said comparing step involves comparing the polarity of the resonant amplitude detected at a first time with the polarity of the resonant amplitude detected at a second later time, wherein a polarity change at the fracture site indicates progress in the healing process.

7. The method of claim 3, wherein said producing step comprises the step of exciting said coil means at a resonant frequency using an oscillator means, and wherein said detecting step comprises the step of detecting changes in the resonant frequency caused by variations in said mutual inductance.

8. The method of claim 7, wherein said comparing step involves comparing the resonant frequency detected at a first time with the resonant frequency detected at a second later time, wherein a decrease in the resonant frequency indicates a decrease in impedance.

9. The method of claim 3, wherein said producing step further comprises the step of providing relative motion between the limb containing the broken bone and said coil means until said coil means is surrounding said fracture site.

10. A method of bone fracture localization, comprising the steps of:
    noninvasively measuring the impedance of bone and other biological matter at a plurality of localized regions along a bone; and,
    comparing said impedance measurements to determine the location of a higher impedance region indicating a fracture site on said bone, wherein noninvasively measuring impedance for each of said plurality of regions comprises the following steps:
    producing an oscillating magnetic field that is spatially concentrated in a localized region along said bone using a coil means, whereby eddy currents induce a secondary magnetic emission which alters the mutual inductance of said coil means in accordance with the impedance of bone and other biological matter in said region; and,
    detecting a change in the mutual inductance of said coil means, wherein an increase in mutual inductance indicates an increase in impedance and a decrease in mutual inductance indicates a decrease in impedance.

11. The method of claim 10, wherein said producing step comprises the step of exciting said coil means at a resonant frequency using an oscillator means, wherein said detecting step comprises the step of detecting changes in resonant amplitude caused by variations in said mutual inductance, and wherein said comparing step comprises the step of comparing the resonant amplitude at each of said localized regions, wherein a higher resonant amplitude will indicate a higher impedance region.

12. The method of claim 10, wherein said producing step comprise the step of exciting said coil means at a resonant frequency using an oscillator means, wherein said detecting step comprises the step of detecting changes in the resonant frequency caused by variations in said mutual inductance, and wherein said comparing step comprises the step of comparing the resonant frequency at each of said localized regions, wherein a higher resonant frequency will indicate a higher impedance region.

13. The method of claim 10, wherein said producing step further comprises the step of moving said coil means having an inner magnetic core relative to the surface of said patient's body until a location proximal to a bone fracture is reached.

* * * * *